(12) United States Patent
Kauppinen et al.

(10) Patent No.: US 11,191,978 B2
(45) Date of Patent: *Dec. 7, 2021

(54) APPARATUS AND METHOD USING AUTOMATIC GENERATION OF A BASE DOSE

(71) Applicant: Varian Medical Systems International AG, Steinhausen (CH)

(72) Inventors: Juha Kauppinen, Espoo (FI); Janne I. Nord, Espoo (FI)

(73) Assignee: Varian Medical Systems International AG, Steinhausen (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/364,806

(22) Filed: Mar. 26, 2019

(65) Prior Publication Data

US 2019/0217122 A1 Jul. 18, 2019

Related U.S. Application Data

(63) Continuation of application No. 14/865,703, filed on Sep. 25, 2015, now Pat. No. 10,252,081.

(51) Int. Cl.
*A61N 5/10* (2006.01)

(52) U.S. Cl.
CPC .............. *A61N 5/1031* (2013.01); *A61N 5/10* (2013.01); *A61N 5/103* (2013.01); *A61N 5/1038* (2013.01); *A61N 5/1042* (2013.01); *A61N 5/1045* (2013.01); *A61N 5/1047* (2013.01); *A61N 2005/1041* (2013.01)

(58) Field of Classification Search
CPC ........ A61N 5/10; A61N 5/103; A61N 5/1031; A61N 5/1038; A61N 2005/1041; A61N 5/1042; A61N 5/1045; A61N 5/1047
USPC .......................................................... 378/65
See application file for complete search history.

(56) References Cited

U.S. PATENT DOCUMENTS

| | | | |
|---|---|---|---|
| 5,647,663 A * | 7/1997 | Holmes | A61N 5/1031 600/407 |
| 6,029,079 A | 2/2000 | Cox | |
| 6,038,283 A | 3/2000 | Carol | |
| 6,142,925 A | 11/2000 | Siochi | |
| 6,222,905 B1 * | 4/2001 | Yoda | A61N 5/1031 378/64 |
| 6,260,005 B1 | 7/2001 | Yang | |
| 6,393,096 B1 | 5/2002 | Carol | |
| 6,546,073 B1 | 4/2003 | Lee | |
| 6,560,311 B1 | 5/2003 | Shepard | |
| 6,661,870 B2 | 12/2003 | Kapatoes | |
| 6,735,277 B2 * | 5/2004 | McNutt | A61N 5/1031 378/64 |

(Continued)

*Primary Examiner* — Allen C. Ho
(74) *Attorney, Agent, or Firm* — Fitch, Even, Tabin & Flannery LLP

(57) ABSTRACT

A control circuit forms a radiation therapy treatment plan by automatically generating a base dose that references dosing information from multiple sources and then using that base dose to optimize a radiation therapy treatment plan. That radiation therapy treatment plan is then used to administer radiation therapy to a patient. That automatically generated base dose can represent any or all of earlier radiation therapy treatments for the patient, a same fraction as a dose presently being optimized per the radiation therapy treatment plan, and future planned fractions for the patient.

16 Claims, 1 Drawing Sheet

(56) References Cited

U.S. PATENT DOCUMENTS

| | | |
|---|---|---|
| 6,792,074 B2 | 9/2004 | Erbel |
| 7,162,008 B2 | 1/2007 | Earl |
| 7,266,176 B2 | 9/2007 | Allison |
| 7,302,033 B2 | 11/2007 | Carrano |
| 7,362,848 B2 | 4/2008 | Saracen |
| 7,450,687 B2 | 11/2008 | Yeo |
| 7,519,150 B2 | 4/2009 | Romesberg, III |
| 7,551,717 B2 | 6/2009 | Tome |
| 7,567,694 B2 | 7/2009 | Lu |
| 7,574,251 B2 | 8/2009 | Lu |
| 7,590,219 B2 | 9/2009 | Maurer, Jr. |
| 7,609,809 B2 | 10/2009 | Kapatoes |
| 7,639,854 B2 | 12/2009 | Schnarr |
| 7,643,661 B2 | 1/2010 | Ruchala |
| 7,693,257 B2 | 4/2010 | Allison |
| 7,734,010 B2 | 6/2010 | Otto |
| 7,773,788 B2 | 8/2010 | Lu |
| 7,801,270 B2 | 9/2010 | Nord |
| 7,809,107 B2 | 10/2010 | Nord |
| 7,817,778 B2 | 10/2010 | Nord |
| 7,831,289 B2 | 11/2010 | Riker |
| 7,853,476 B2 | 12/2010 | Reiner |
| 7,970,624 B2 | 6/2011 | Anderson |
| 8,009,804 B2 | 8/2011 | Siljamaki |
| 8,085,899 B2 | 12/2011 | Nord |
| 8,121,252 B2 | 2/2012 | Nord |
| 8,180,020 B2 | 5/2012 | Kilby |
| 8,222,616 B2 | 7/2012 | Lu |
| 8,232,535 B2 | 7/2012 | Olivera |
| 8,249,215 B2 | 8/2012 | Vaitheeswaran |
| 8,284,897 B2 | 10/2012 | Nord |
| 8,295,436 B2 | 10/2012 | Nord |
| 8,331,532 B2 | 12/2012 | Nord |
| 8,363,784 B2 | 1/2013 | Sobering |
| 8,406,844 B2 | 3/2013 | Ruchala |
| 8,412,544 B2 | 4/2013 | Reiner |
| 8,442,287 B2 | 5/2013 | Fordyce, II |
| 8,509,383 B2 | 8/2013 | Lu |
| 8,538,776 B2 | 9/2013 | Reiner |
| 8,644,571 B1 | 2/2014 | Schulte |
| 8,693,630 B2 | 4/2014 | Nord |
| 8,699,664 B2 * | 4/2014 | Otto ............... A61N 5/1067 378/65 |
| 8,767,917 B2 | 7/2014 | Ruchala |
| 8,774,358 B2 | 7/2014 | Zankowski |
| 8,836,697 B2 | 9/2014 | Nord |
| 8,961,382 B2 | 2/2015 | Nord |
| 8,986,186 B2 | 3/2015 | Zhang |
| 9,044,601 B2 | 6/2015 | Currell |
| 9,089,696 B2 | 7/2015 | Verhaegen |
| 9,123,097 B2 | 9/2015 | Lee |
| 9,155,907 B2 | 10/2015 | Kauppinen |
| 9,192,782 B1 | 11/2015 | Grimm |
| 9,192,786 B2 | 11/2015 | Van |
| 9,275,189 B2 | 3/2016 | Walker |
| 9,275,451 B2 | 3/2016 | Ben-Haim |
| 9,381,376 B2 | 7/2016 | Toimela |
| 9,387,345 B2 | 7/2016 | Nord |
| 9,403,035 B2 | 8/2016 | Gum |
| 9,409,039 B2 | 8/2016 | Hartman |
| 9,421,397 B2 | 8/2016 | Purdie |
| 9,454,823 B2 | 9/2016 | Zankowski |
| 9,463,334 B2 | 10/2016 | Kuusela |
| 9,468,776 B2 | 10/2016 | Fredriksson |
| 9,507,886 B2 | 11/2016 | Fiege |
| 9,679,110 B2 | 6/2017 | Moore |
| 9,731,147 B2 | 8/2017 | Nord |
| 9,731,148 B2 | 8/2017 | Olivera |
| 9,764,162 B1 | 9/2017 | Willcut |
| 9,827,445 B2 | 11/2017 | Marcos |
| 9,907,979 B2 | 3/2018 | Nord |
| 9,925,391 B2 | 3/2018 | Carpenter |
| 9,987,504 B2 | 6/2018 | Nord |
| 10,039,936 B2 * | 8/2018 | Nord ............... A61N 5/1031 |
| 10,046,177 B2 * | 8/2018 | Sjölund ............ A61B 6/032 |
| 10,058,714 B2 * | 8/2018 | Hårdemark ........ A61N 5/103 |
| 10,076,673 B2 * | 9/2018 | Ranganathan ..... A61N 5/1031 |
| 10,137,314 B2 * | 11/2018 | Fredriksson ...... A61N 5/1037 |
| 10,146,393 B2 * | 12/2018 | Nord ............... G06F 3/048 |
| 10,252,081 B2 | 4/2019 | Kauppinen |
| 10,384,080 B2 * | 8/2019 | Eriksson .......... A61N 5/1031 |
| 10,441,811 B2 * | 10/2019 | Isola ............... A61N 5/1048 |
| 10,449,388 B2 * | 10/2019 | Yin ................. A61N 5/1031 |
| 10,549,121 B2 * | 2/2020 | Wu ................. A61N 5/1039 |
| 10,589,127 B2 * | 3/2020 | Nord ............... A61N 5/103 |
| 10,603,511 B2 * | 3/2020 | Bzdusek .......... G16H 20/40 |
| 10,675,483 B2 * | 6/2020 | Vik ................. A61N 5/1031 |
| 10,762,167 B2 * | 9/2020 | Hartman .......... A61N 5/103 |

* cited by examiner

APPARATUS AND METHOD USING AUTOMATIC GENERATION OF A BASE DOSE

CROSS-REFERENCE TO RELATED APPLICATION

This application is a continuation of prior U.S. patent application Ser. No. 14/865,703, filed Sep. 25, 2015, now U.S. Pat. No. 10,252,081 B2 issued on Apr. 9, 2019, which is incorporated herein by reference in its entirety.

TECHNICAL FIELD

These teachings relate generally to the use of radiation as a therapeutic treatment and more specifically to the formation and use of corresponding radiation-treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient using a specific radiation therapy treatment platform. Such treatment plans are often optimized prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using a variety of automatically-modified (i.e., "incremented") treatment plan optimization parameters.

Treatment plans are typically generated as a function of user-specified dosimetric goals. In many cases dose optimization proceeds as a function of both a presently-planned dose (i.e., the dose being optimized for a particular radiation treatment session) and a so-called base dose. The base dose is an aggregated per-patient metric representing the radiation dosage received in earlier radiation treatment sessions (if any), during the same day (i.e., "fraction") (if any) as the session currently being optimized, and future sessions as well (if any).

These references to previous and future dosings for a particular patient generally refer to dosings that are administered as part of an overall unified and integrated effort to treat a particular unwanted biological condition such as a tumor or group of tumors. Accordingly, and usually, it is not contemplated that the base dose will include radiation dosings that might have nothing to do with the present course of treatment such as, for example, dentistry x-rays. That said, however, in some cases it may be appropriate to include ancillary exposures of radiation (such as a series of x-rays to view and diagnosis a broken bone or a CT scan to diagnose some other unrelated condition) when computing the base dose.

A typical prior art practice is to manually calculate the base dose by combining dose distributions from their corresponding different events. Such an approach, of course, is prone to human error, oversight, misinterpretations, and misunderstandings, all of which can lead to an inaccurate base dose. An incorrect base dose, in turn, can lead to a sub-optimum radiation treatment plan.

BRIEF DESCRIPTION OF THE DRAWINGS

The above needs are at least partially met through provision of the apparatus and method using automatic generation of a base dose described in the following detailed description, particularly when studied in conjunction with the drawings, wherein.

Figure 1:
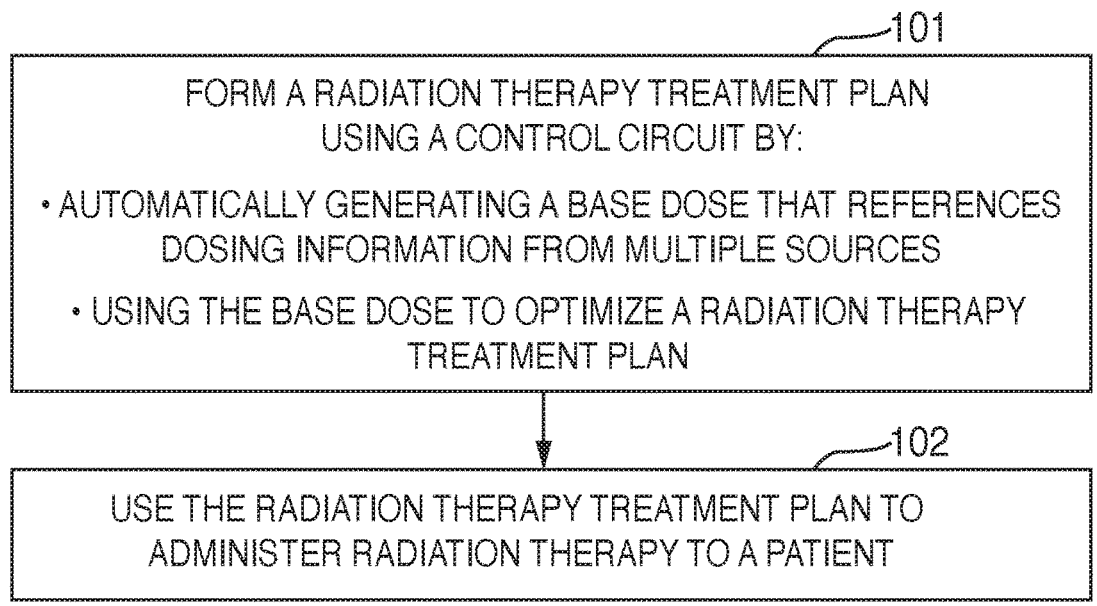
FIG. 1 comprises a flow diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit forms a radiation therapy treatment plan by automatically generating a base dose that references dosing information from multiple sources and then using that base dose to optimize a radiation therapy treatment plan. That radiation therapy treatment plan is then used to administer radiation therapy to a patient. That automatically generated base dose can represent any or all of earlier radiation therapy treatments for the patient, a same fraction as a dose presently being optimized per the radiation therapy treatment plan, and future planned fractions for the patient.

By one approach the control circuit generates the base dose as a function of a particular treatment model such that the base dose is suitable for present use in optimizing the radiation therapy treatment plan. In any event, the control circuit uses this base dose to optimize a radiation therapy treatment plan by, at least in part, using the base dose to limit an accumulation of radiation in a particular volume of the patient.

These teachings are highly flexible in practice and will accommodate various modifications and variations. For example, the aforementioned multiple sources can include any one or more of treatment records for radiation therapy treatment previously delivered to the patient, radiation therapy treatment plans for undelivered parallel treatment for the patient, patient images, and patient deformation information, with other sources being possible depending upon the specifics of a particular application setting.

As another example of the flexibility of these teachings, by one approach the control circuit can individually weight the dosing information from different sources. Such weighting can reflect, for example, an actual or perceived relevancy of the source and/or accuracy of the source. In lieu of the foregoing or in combination therewith, when producing a base dose per these teachings the control circuit can also produce a corresponding indication of uncertainty. That indication of uncertainty can then be used when optimizing the radiation therapy treatment plan.

So configured, these teachings facilitate efficiently and reliably accounting for both delivered and undelivered dosings when optimizing a radiation treatment plan for a particular patient. As one simple example in these regards, the automatically-calculated base dose can be used in optimization to limit an aggregate accumulated dose in one or more target volumes and untargeted volumes for a particular patient.

Figure 2:
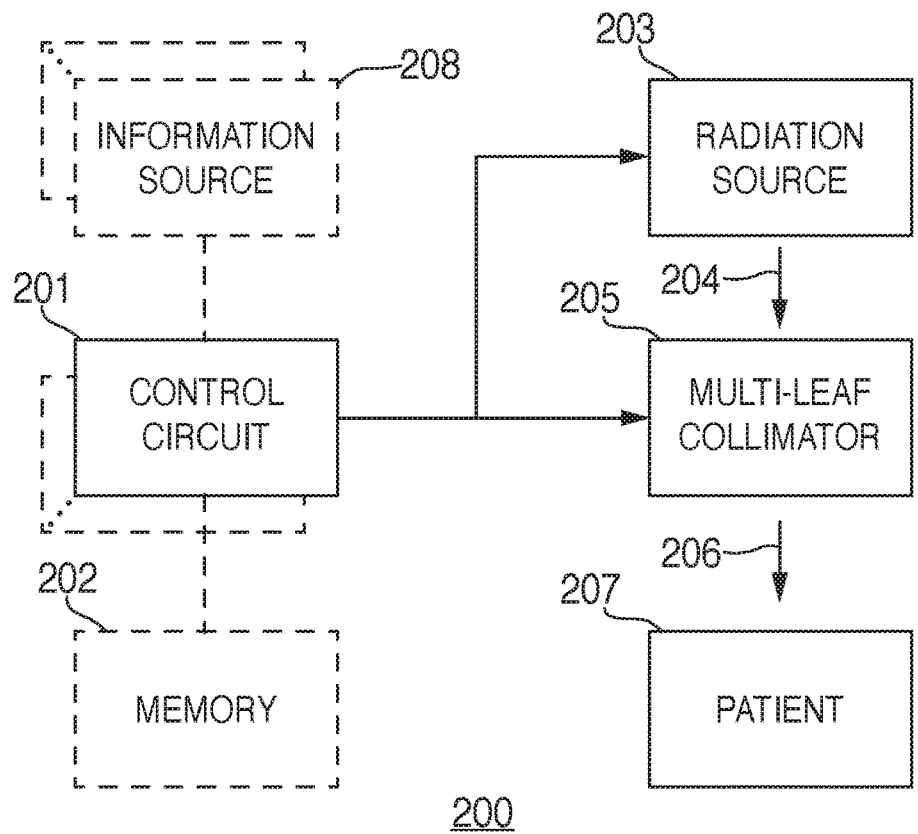
FIG. 2 comprises a block diagram as configured in accordance with various embodiments of these teachings.

These and other benefits may become clearer upon making a thorough review and study of the following detailed description. Referring now to the drawings, and in particular to FIG. 1, an illustrative process 100 that is compatible with many of these teachings will now be presented. For the sake of an illustrative example it will be presumed in this description that a control circuit (or plurality of control circuits) carries out the actions, steps, and functions described in this process 100. FIG. 2 provides an illustrative example in these regards.

As shown in FIG. 2, a radiation therapy treatment platform 200 can include or otherwise operably couple to a control circuit 201. Being a "circuit," the control circuit 201 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 201 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here.

This control circuit 201 is configured (for example, by using corresponding programming as will be well understood by those skilled in the art) to carry out one or more of the steps, actions, and/or functions described herein. It will also be understood that a "control circuit" can comprise multiple such components or platforms as suggested by the phantom control circuit box shown in FIG. 2.

By one optional approach the control circuit 201 operably couples to a memory 202. This memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

In addition to radiation treatment plans, dosing information from various sources, and/or base dose information itself, this memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The radiation therapy treatment platform 200 also includes a therapeutic radiation beam source 203 that operably couples and responds to the control circuit 201. So configured, a corresponding radiation beam 204 as emitted by the therapeutic radiation beam source 203 can be selectively switched on and off by the control circuit 201. These teachings will also accommodate having the control circuit 201 control the relative strength of the radiation beam 204. Radiation sources are well understood in the art and require no further description here.

In this example the radiation beam 204 is directed towards a multi-leaf collimator 205 that also operably couples to the control circuit 201 to thereby permit the control circuit 201 to control movement of the collimator's leaves and hence the formation and distribution of one or more radiation-modulating apertures. Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically the leaves of a multi-leaf collimator are organized in pairs that are aligned collinearly with respect to one another and that can selectively move towards and away from one another via controlled motors.

By passing radiation beam 204 through the aperture(s) of a multi-leaf collimator 205 the radiation beam 204 can be modulated to provide a modulated radiation beam 206 that better matches the dosing requirements of the treatment session. These dosing requirements typically include (or at least presume) prescribing which body tissues to irradiate and which body tissues to avoid irradiating. The resultant modulated radiation beam 206 then reaches a treatment target in a corresponding patient 207.

In this illustrative example the control circuit 201 may optionally also operably couple to one or more information sources 208. As will be discussed further below, these information sources 208 may contain dosing information pertaining to the patient 207. That dosing information can comprise, but is not limited to, past, present, and/or future radiation-exposure events for the patient 207. The information sources 208 themselves may comprise a variety of information-harboring platforms (including but not limited to computers, memories, databases, servers, and the like) or can even comprise the aforementioned control circuit 201 and/or memory 202 themselves.

With continuing reference to both FIGS. 1 and 2, this process 100 begins, at block 101, with using the control circuit 201 to form a radiation therapy treatment plan. This activity includes automatically generating a base dose that references dosing information from multiple sources. By one approach, if desired, this activity can comprise generating the base dose as a function of a particular treatment model such that the base dose is suitable (i.e., compatible or normalized) for present use in optimizing this particular radiation therapy treatment plan. For example, biological modeling can serve to estimate a single dose distribution having a same biological effect as a combined effect of the multiple sources.

Regardless of how ultimately represented, the generated base dose will typically serve to represent at least two of one or more earlier radiation therapy treatments for this patient 207, a same fraction as a dose presently being optimized per the radiation therapy treatment plan, and future planned fractions for the patient 207 per the present overall radiation treatment regimen. In a typical application setting all of these dosing events constitute an integral part of the same overall radiation treatment regimen. That said, if desired, other dosing events can be included if desired, including, for example, dosing owing to imaging events and the like.

As noted above, the foregoing dosing information is accessed from (directly or directly) a plurality of sources. These teachings will accommodate receiving such information from a variety of different sources of the same type. These teachings will also accommodate a variety of different types of sources including, but not limited to, treatment records for radiation therapy treatment previously delivered to the patient 207 (including but not limited to radiation therapy treatment plans for previously-delivered dosings), radiation therapy treatment plans for undelivered parallel treatment for the patient 207, and patient images (where, for example, the control circuit can ascertain from the image, either directly or indirectly, which volumes of the patient 207 were exposed to imaging radiation and from what relative angle(s)).

These teachings will also accommodate using patient deformation information as a source. When treatment planning (including plan optimization) is being performed, it is usual that a relatively recent patient image is used as basis for the treatment plan generation. If the patient 207 has received a previous dose or has a future planned dose that is defined in an earlier/other patient image (with different patient geometry), the dose distribution(s) suitable for being used as a base dose can to be brought to the new patient image (which is used for the plan optimization). A deformable registration can be a vector field that describes how two geometries are related. The vector field can be used, for example, for sampling dose levels from the first geometry to the second geometry. Therefore, when a deformable registration is available, it is possible to optimize a treatment dose for a cell in a (new) patient image which (cell) is known to have accumulated a certain dose level in another (earlier/other) patient geometry.

Generally speaking, once all of the dosing information has been retrieved from these various sources, that dosing information can be summed to generate the base dose. If desired, the control circuit 201 can be further configured to assess and compare these various discrete dosing events and/or sources to identify possibly redundant content. If and when redundant or otherwise overlapping dosing information exists, the control circuit can, for example, delete redundant information to avoid overestimating the base dosage. By one approach, when information is available to assess precision and/or accuracy, the control circuit 201 can delete redundant information that is characterized as being the least reliable. By another approach, the control circuit 201 can be configured to calculate an average for any instances of redundant information and utilize that resultant average as the representative dosing value.

The control circuit 201 then utilizes that automatically calculated base dose to optimize a radiation therapy treatment plan. For example, the control circuit 201 can use the calculated base dose to limit an accumulation of radiation in one or more volumes of the patient 207 including both treatment targets and untargeted areas where radiation is preferably avoided.

By one approach, where, for example, the control circuit 201 has information regarding relevancy of a particular source of dose information and/or accuracy of a particular source of dose information, the control circuit 201 can individually weight the dosing information from various sources to reflect that sense of relevancy and/or accuracy. That weighting can then serve to provide a basis for also developing a corresponding indication of uncertainty regarding the generated base dose. When available, that indication of uncertainty can be utilized when optimizing the radiation therapy treatment plan. For example, the optimization parameters may be set to favor observing the highest possible base dose but to permit using lower base doses if necessary to achieve one or more other treatment plan objectives.

So configured, these teachings can facilitate not only automatically calculating a base dose that can be reliably and effectively used when optimizing a corresponding radiation treatment plan, but can help resolve uncertainties that can arise when facing conflicting metrics that purport to represent a same dosing event and or that can help accommodate uncertainties regarding the accuracy of the original data. Overall, these teachings can reduce the time required to calculate a usable base dose while simultaneously helping to ensure the accuracy of the calculated result and hence the integrity of the resultant optimized radiation treatment plan.

At block 102 that radiation therapy treatment plan can then be used to administer radiation therapy to a patient 207.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method comprising:
   forming a radiation therapy treatment plan using a control circuit by:
   automatically generating a base dose that references dosing information from multiple sources by, at least in part, individually weighting the dosing information from the multiple sources; and
   using the base dose to optimize a radiation therapy treatment plan; and
   using the radiation therapy treatment plan to administer a radiation therapy treatment to a patient.

2. The method of claim 1, wherein the base dose represents at least two of:
   earlier radiation therapy treatments for the patient;
   a same fraction as a dose presently being optimized per the radiation therapy treatment plan; and
   future planned fractions for the patient.

3. The method of claim 1, wherein automatically generating a base dose that references dosing information from multiple sources comprises, at least in part, generating the base dose as a function of a particular treatment model such that the base dose is suitable for present use in optimizing the radiation therapy treatment plan.

4. The method of claim 1, wherein using the base dose to optimize a radiation therapy treatment plan comprises, at least in part, using the base dose to limit an accumulation of radiation in a particular volume of the patient.

5. The method of claim 1, wherein the multiple sources include at least one of:
   treatment records for a radiation therapy treatment previously delivered to the patient;
   radiation therapy treatment plans for an undelivered parallel radiation therapy treatment for the patient;
   patient images; and
   patient deformation information.

6. The method of claim 1, wherein individually weighting the dosing information from the multiple sources comprises individually weighting the dosing information as a function, at least in part, of at least one of:
   relevancy of a source of the multiple sources; and
   accuracy of a source of the multiple sources.

7. The method of claim 1, wherein automatically generating a base dose that references dosing information from multiple sources comprises, at least in part, producing a base dose and a corresponding indication of uncertainty.

8. The method of claim 1, wherein automatically generating a base dose that references dosing information from multiple sources comprises using biological modeling to estimate a single dose distribution having a same biological effect as a combined effect of the multiple sources.

9. An apparatus comprising:
   a control circuit configured to form a radiation therapy treatment plan by:
   automatically generating a base dose that references dosing information from multiple sources by, at least in part, individually weighting the dosing information from the multiple sources; and
   using the base dose to optimize a radiation therapy treatment plan; and
   a radiation therapy treatment platform configured to use the radiation therapy treatment plan to administer a radiation therapy treatment to a patient.

10. The apparatus of claim 9, wherein the base dose represents at least two of:
    earlier radiation therapy treatments for the patient;
    a same fraction as a dose presently being optimized per the radiation therapy treatment plan; and
    future planned fractions for the patient.

11. The apparatus of claim 9, wherein the control circuit is configured to automatically generate the base dose that references dosing information from multiple sources by, at least in part, generating the base dose as a function of a particular treatment model such that the base dose is suitable for present use in optimizing the radiation therapy treatment plan.

12. The apparatus of claim 9, wherein the control circuit is configured to use the base dose to optimize a radiation therapy treatment plan by, at least in part, using the base dose to limit an accumulation of radiation in a particular volume of the patient.

13. The apparatus of claim 9, wherein the multiple sources include at least one of:
    treatment records for a radiation therapy treatment previously delivered to the patient;
    radiation therapy treatment plans for an undelivered parallel radiation therapy treatment for the patient;
    patient images; and
    patient deformation information.

14. The apparatus of claim 9, wherein the control circuit is configured to individually weight the dosing information from the multiple sources by individually weighting the dosing information as a function, at least in part, of at least one of:
    relevancy of a source of the multiple sources; and
    accuracy of a source of the multiple sources.

15. The apparatus of claim 9, wherein the control circuit is configured to automatically generate a base dose that references dosing information from multiple sources by, at least in part, producing a base dose and a corresponding indication of uncertainty.

16. The apparatus of claim 9, wherein the control circuit is configured to automatically generate a base dose that references dosing information from multiple sources by using biological modeling to estimate a single dose distribution having a same biological effect as a combined effect of the multiple sources.

* * * * *